United States Patent [19]

Cummings et al.

[11] Patent Number: 5,187,196
[45] Date of Patent: Feb. 16, 1993

[54] GRAZING REPELLENT FOR GEESE AND SWANS

[75] Inventors: John L. Cummings, Lakewood, Colo.; James R. Mason, Bridgeton; Ralph M. Trksak, Manville, both of N.J.

[73] Assignee: The United States of America as represented by the Secretary of Agriculture, Washington, D.C.

[21] Appl. No.: 322,039

[22] Filed: Mar. 13, 1989

[51] Int. Cl.$^5$ .......................................... A01N 37/12
[52] U.S. Cl. .................................... 514/535; 514/778; 514/918
[58] Field of Search .................. 514/535, 728, 918; 560/19

[56] References Cited

U.S. PATENT DOCUMENTS

| | | | |
|---|---|---|---|
| 2,967,128 | 1/1961 | Kare | 514/535 |
| 4,582,922 | 4/1986 | Meier | 560/19 |
| 4,790,990 | 12/1988 | Mason et al. | 514/535 |
| 4,812,445 | 3/1989 | Eden et al. | 514/778 |

*Primary Examiner*—Frederick E. Waddell
*Assistant Examiner*—Kevin E. Weddington
*Attorney, Agent, or Firm*—M. Howard Silverstein; John D. Fado

[57] ABSTRACT

Geese and swans are repelled by applying methyl anthranalate or dimethyl anthranalate to their habitats or to pelleted agricultural chemicals lethal to geese or swans. With regard to applying the repellent to habitats, preferably the repellent is encapsulated in a starch-based material that is water tolerant and provides time release of the repellent.

22 Claims, No Drawings

GRAZING REPELLENT FOR GEESE AND SWANS

FIELD

This invention relates to repelling geese and swans.

PRIOR ART

Previously it has been shown, in U.S. Pat. Nos. 2,967,128 and 4,790,990, that dimethyl anthranilate (DMA), methyl anthranilate (MA) and closely related compounds are repellents for some avian species when incorporated in or sprayed on foodlots or food crops. All the birds described in these patents are known to respond to taste and flavor cues.

SUMMARY

It now has been unexpectedly discovered that geese and swans, species that are notoriously indifferent to taste and flavor cues, are repelled by DMA and MA. When a habitat is treated with the repellent, the birds may attempt to graze in the area, but will discontinue feeding upon "tasting" the DMA or MA. Additionally, the birds may avoid treated areas without attempting to graze thereon, which is a further unexpected aspect of the invention.

Still further, the present invention provides an encapsulated form of the repellent which permits use under field conditions in which wetting might occur. All previous MA and DMA encapsulation matrices rapidly degraded when moistened. Broadly, this aspect of the invention comprises applying the repellent to the target habitat while encapsulated in a water-insoluble, time release, edible starch matrix.

It also has been unexpectedly discovered that MA is more effective than DMA, which is the opposite of the prior art teachings as to taste-sensitive birds.

DETAILED DESCRIPTION

In the practice of the present invention the DMA and MA may be applied to bird habitats in a conventional manner. For example, liquid carriers may be employed, and the repellent may be sprayed on the target substrate. This technique is old in the art as shown by U.S. Pat. No. 2,967,128. Water can be used as the major portion of the liquid carrier by forming a suspension or emulsion of the repellent by the use of small amounts of an emulsifying agent, or a gum such as gum acacia, or gum tragacanth. Exemplary emulsifying agents are polyoxyethylene sorbitan monolaurate, monostearate, tristearate, monooleate.

A water solution of the repellent also can be prepared by the use of a suitable co-solvent, i.e., an organic solvent which will dissolve the repellent chemical and which is freely miscible with water. Whatever organic solvent is employed, solvents that may damage the birds' habitats obviously should be avoided. Propylene glycol is an exemplary solvent.

Concentrations of DMA and MA in the liquid carrier generally may range from about 20 to 22 parts repellent per 100 parts of carrier.

The incorporation of materials such as gum acacia may assist in adhering the repellent to the target surface.

Solid carriers also may be employed. For example, the repellent may be entrapped in or absorbed on a solid matrix. The incorporation of DMA or MA in a solid matrix is known in the art. Examples of this would include microencapsulation, extrusion, fluidized bed drying, drum drying, spray drying or any other liquid-in-solid entrapment technique.

Microencapsulation may be performed in accordance with U.S. Pat. No. 3,455,838. In the exemplary formation of microcapsules, a droplet of repellent is encapsulated in for example a polymer, the thickness of which may be varied to change the diffusion rate of the repellent; or the coating of polymer or equivalent material may be so thick that the repellent will escape only when a bird crushes the microbead during feeding.

With regard to spray drying, typically the repellent-to-solid matrix ratio should be about 5-55% by weight repellent, more commonly 15-22% by weight.

Solid matrices which may be suitable for use in entrapping MA or DMA include gelatin, gum arabic, or certain modified food starches, as well as plasticizing agents such as malto dextrin, lactose, dextrin, corn syrup solids, and combinations of same.

Optionally, the repellent may be absorbed on the surface of solid particles or pellets; or laminates may be formed of alternating layers of repellent and solid material such as starch (this latter system sometimes is referred to as enrobing).

Ultraviolet blocking agents may be included in the carrier compositions, for obvious purposes, because anthranilate derivatives are photoreactive.

Encapsulation is the preferred vehicle for the repellent. The following encapsulation formulation is particularly effective in that it avoids rapid degradation when moistened. Broadly it comprises a water-insoluble, time release, edible starch matrix. Preferably, the material is a high amylose starch containing at least 50% by weight amylose or a starch which has been dispersed in salt solution before encapsulation.

To form this particularly effective starch-encapsulated product, the repellent is combined with a high temperature-stabilized dispersion of starch, optionally containing salt. The temperature-stabilized starch dispersion acts as a protective colloid, encasing the material to be encapsulated. Upon subsequent rapid cooling of this mixture on a chilled rotating drum, the starch polymer chains collapse upon themselves, forming a firm sheet and encapsulating the core material. The sheet can then be cut, chopped, or sliced in the wet state, then dried and ground to yield particles. In the resultant product, the material being encapsulated is evenly distributed throughout the starch matrix. This encapsulation process comprises the following steps:

1) slurrying the starch in water, optionally in the presence of salt;

2) thoroughly dispersing the starch in the slurry by injecting steam at a pressure of at least 110 psi into the slurry to raise its temperature to 120° to 180° C. at a pressure of 55-120 psi or above;

3) adding to the dispersion the material to be encapsulated and effecting intimate mixing of the latter therein;

4) spreading the resultant mixture on a chilled surface such as a chilled revolving drum or a continuous belt;

5) recovering the encapsulated material in sheet form; and 6) cutting or grinding and drying the resultant matrix of starch and encapsulated material.

Any starch material such as corn starch, rice starch, potato starch, tapioca starch, wheat starch, amylose or amylpectin fractions may be employed in preparing the encapsulated starch matrix. Additionally, the starch base may be modified or unmodified. It is preferred, however, to use a high amylose starch, i.e., one containing at least 50% by weight amylose, and more preferably a starch containing at least 70% by weight of amylose. When using starches containing less than 50% of amylose content, it is necessary for the addition of salt to the starch slurry. Suitable salts for this use include ammonium sulfate, ammonium monobasic or dibasic phosphate, magnesium sulfate, sodium sulfate and mixtures thereof.

In addition to the use of starch as the encapsulating material, water soluble hydrocolloids such as polyvinyl alcohol, carboxymethylcellulose, hydroxyethylcellulose, polyacrylic acid and polyvinyl pyrrolididone may replace up to 50% of the starch component.

The need for salt, as well as the ratio of salt, starch and water, in the slurry are dependent upon the starch selected. Those starches containing high levels of amylose require little or no salt to effect efficient setting on the chilled surface while the low amylose starches such as amylopectin based starches or dextrins may require saturated or super-saturated levels at the exit temperature. Similarly, the level of amylose in the starch affects the choice and concentration of the salt required for efficient precipitation, with the higher amylose containing starches, i.e., greater than 50% amylose, capable of forming a firm sheet with any concentration of any of the salts mentioned above, while the starches with lower levels of amylose, i.e., less than 50%, require higher levels of the preferred salts such as ammonium sulfate and magnesium sulfate for efficient precipitation rates. The amount of starch usually varies from about 20 to 40% by total weight of the slurry (starch, salt if present and water). The amount of salt employed should be kept as low as possible, generally in the range of 10 to 20% by total weight of the slurry (starch, salt if present, and water) since some of the salt employed will remain in the final starch matrix. In all cases, the levels of the components should be such that the starch/salt/water ratio does not cause retrogradation prior to setting on the chilled surface.

EXAMPLE

High amylose starch (Hylon VII, National Starch and Chemical) containing approximately 70% amylose was slurried in water at 35% anyhydrous solids. Sodium stearyl lactylate was added to a concentration of 0.1 percent on total weight. This slurry was processed through a jet cooker at 175°-100° C. and then piped to a vertical flash chamber where temperatures were maintained at 120°-125° C. Dimethyl anthranilate (DMA) was metered into the hot starch cook after the flash chamber at a rate chosen to give 30 percent DMA on anhydrous starch and DMA weight. The DMA/starch mix was emulsified in-line using a turbine pump. Exit temperature after emulsification was 85°-92° C.

After exiting the turbine pump, the starch DMA emulsion was spread by an applicator blade onto the surface of a chilled drum in an approximately ¼th inch coating. It rapidly set to a firm opaque white sheet. The cool sheet was removed from the drum by a doctor blade and cut to approximately ¼ inch cubes with a Comitrol cutter (Ureeschel laboratories). These cubes were dried in a Uni-Glass fluid bed dried (Glass Air Techniques).

Composition of the dried sheet which retained 94% of the added DMA was shown by analysis to be:

| | | |
|---|---|---|
| Starch | 62.3% | (on total matter) |
| DMA | 24.7% | (28.4% on dry matter) |
| water | 13.0% | |

When 10 grams of the encapsulated DMA was stored in 100 ml. of distilled water for 7 days, only 9% of the encapsulated material was lost.

More details of a procedure to produce the preferred encapsulated product of the present invention are disclosed in U.S. Pat. No. 4,812,445.

Whatever carrier is employed in the practice of the present invention, the repellent generally is applied to the habitat in an amount of about 3 to 6 pounds of active ingredient (repellent only) per acre. With such a dosage, the birds either discontinue feeding while grazing in a treated area, or actually avoid the treated area.

Typical habitats for geese and swans include grasses such as turf, winter wheat, and winter rye, wherein the repellent is applied to the grass stems. Other habitats include emerging rice and sprouting crops such as corn or barley. Here to, repellent is applied to the plant.

In addition, the repellent may be applied to pelleted agricultural chemicals which are harmful if not lethal to geese and swans so as to discourage ingestion thereof. Many pelletized agricultural chemicals have a discernible taste or odor so that they are avoided by birds which are taste sensitive. However, geese and swans, which are not regarded as taste sensitive, are apt to ingest such harmful, even lethal materials, in the absence of the presence of MA or DMA. Pelleted agricultural chemicals would include pesticides, herbicides and fertilizers such as carbamates, organophosphates, triazines, substituted ureas, acetanalides, and dinitroanaline.

The repellent may be combined with such pellets by spraying on, or immersing in a solution or suspension of the repellent. Generally, the repellent may be incorporated with the pellet in an amount of about 0.25 to 1.0 parts active ingredient (repellent only) per 100 parts of agricultural pellet.

Geese and swans which may be repelled by the practice of the present invention include Canada geese (*Branta canadensis*), Snow geese (*Chen caerulescens*), Brant (*Branta bernicla*), Barnacle geese (*Branta leucopsis*), and White-fronted geese (*Anser albifrons*), as well as tundra swans (*Cygnus columbianus*), trumpeter swans (*Cygnus buccinator*), and mute swans (*Cygnus olor*).

We claim:

1. A method of repelling geese and swans from habitats for such birds comprising applying a compound selected from the group consisting of dimethyl anthranilate and methyl anthranilate to said habitats in an amount effective to repel geese or swans from said habitats.

2. A method of causing geese and swans to avoid habitats for such birds comprising applying a compound selected from the group consisting of dimethyl anthranilate and methyl anthranilate to said habitats, in an amount effective to cause said geese or swans to avoid said habitats without attempting to graze thereon.

3. The method of claim 1 wherein said compound is methyl anthranilate.

4. The method of claim 1 wherein said habitats are grass.

5. The method of claim 1 wherein said compound is incorporated in a carrier.

6. The method of claim 2 wherein said compound is methyl anthranilate.

7. The method of claim 2 wherein said habitats are grass.

8. The method of claim 2 wherein said compound is incorporated in a carrier.

9. The method of claim 5 wherein said carrier is a liquid carrier.

10. The method of claim 5 wherein said carrier is a solid carrier.

11. The method of claim 8 wherein said carrier is a liquid carrier.

12. The method of claim 8 wherein said carrier is a solid carrier.

13. The method of claim 10 wherein said solid carrier encapsulates said compound.

14. The method of claim 12 wherein said solid carrier encapsulates said compound.

15. The method of claim 13 wherein said habitats are grass.

16. The method of claim 13 wherein said solid carrier comprises a water-insoluble, time release, edible starch matrix.

17. The method of claim 14 wherein said habitats are grass.

18. The method of claim 14 wherein said solid carrier comprises a water-insoluble, time release, edible starch matrix.

19. The method of claim 15 wherein said compound is methyl anthranilate.

20. The method of claim 16 wherein said starch matrix is at least 50% by weight amylose.

21. The method of claim 17 wherein said compound is methyl anthranilate.

22. The method of claim 18 wherein said starch matrix is at least 50% by weight amylose.

* * * * *